025B2

United States Patent
Alvarado

(10) Patent No.: US 10,687,934 B2
(45) Date of Patent: Jun. 23, 2020

(54) SEROUS MEMBRANE FOR OCULAR SURFACE DISORDERS

(71) Applicant: Carlos A. Alvarado, Guatemala (GT)

(72) Inventor: Carlos A. Alvarado, Guatemala (GT)

(73) Assignee: Carlos A. Alvarado, Plano, TX (US)

( * ) Notice: Subject to any disclaimer, the term of this patent is extended or adjusted under 35 U.S.C. 154(b) by 161 days.

(21) Appl. No.: 15/998,292

(22) PCT Filed: Jul. 5, 2016

(86) PCT No.: PCT/IB2016/054024
§ 371 (c)(1),
(2) Date: Aug. 2, 2018

(87) PCT Pub. No.: WO2018/007849
PCT Pub. Date: Jan. 11, 2018

(65) Prior Publication Data
US 2019/0038398 A1    Feb. 7, 2019

(51) Int. Cl.
*A61F 2/14* (2006.01)
*A61L 27/36* (2006.01)
*A61F 9/007* (2006.01)

(52) U.S. Cl.
CPC .......... *A61F 2/142* (2013.01); *A61L 27/3629* (2013.01); *A61F 2/145* (2013.01); *A61F 2/1451* (2015.04); *A61F 9/007* (2013.01); *A61L 2430/16* (2013.01)

(58) Field of Classification Search
CPC .. A61F 2/14; A61F 2/142; A61F 2/145; A61F 2/1451; A61F 9/007; A61L 2430/16; A61L 27/3629
See application file for complete search history.

(56) References Cited

U.S. PATENT DOCUMENTS

| | | |
|---|---|---|
| 174,465 A | 3/1876 | Graham |
| 2,127,903 A | 8/1938 | Bowen |
| 3,272,204 A | 9/1966 | Artandi |
| 3,366,440 A | 1/1968 | Nuwayser |
| 3,425,418 A | 2/1969 | Chvapil |
| 3,562,820 A | 2/1971 | Braun |
| 4,120,649 A | 10/1978 | Schechter |
| 4,772,283 A | 9/1988 | White |
| 4,902,508 A | 2/1990 | Badylak |
| 5,755,791 A | 5/1998 | Whitson |
| 5,997,575 A | 12/1999 | Whitson |
| 6,152,142 A * | 11/2000 | Tseng ............ A01N 1/02 128/898 |
| 6,312,474 B1 | 11/2001 | Francis |
| 6,326,019 B1 | 12/2001 | Tseng |
| 6,869,619 B2 | 3/2005 | Spievack |
| 7,494,802 B2 | 2/2009 | Tseng |
| 7,819,918 B2 | 10/2010 | Malaviya |
| 9,023,342 B2 | 5/2015 | Alvarado |
| 2002/0193886 A1 * | 12/2002 | Claeson ............ A61F 2/14 623/23.72 |
| 2008/0046070 A1 * | 2/2008 | Obermiller ......... A61F 2/2418 623/1.24 |
| 2010/0198348 A1 * | 8/2010 | Hiles ................. A61F 2/142 623/5.16 |
| 2014/0037595 A1 * | 2/2014 | Alvarado ........... A61L 27/3687 424/93.7 |

FOREIGN PATENT DOCUMENTS

| ES | 2172986 T3 | 10/2002 |
|---|---|---|
| SU | 112891 A1 | 12/1984 |

OTHER PUBLICATIONS

Andriani F. (2003) Analysis of Microenvironmental Factors Contributing to Basement Membrane Assembly and Normalized Epidermal Phenotype Journal of Investigative Dermatology 120, 923-931; doi:10.1046/j.1523-1747.2003. 12235.
Batmanov I, et al. (1990) Use of fresh amnion in the treatment of corneal diseases. Vestnik Oftalmologii 106(5):17-9.
Baum J (2002) Thygeson lecture. amniotic membrane transplantation: why is it effective? Cornea 21:339-341.
Chen J, et al. (2000) A clinical study on fresh amniotic membrane transplantation for treatment of severe ocular surface disorders at acute inflammatory and cicatricial stage]. Zhonghua Yan Ke Za Zhi 36:13-7, 1.
Dua HS, et al. (2004) the amniotic membrane in ophthalmology. Surv Ophthalmol 49:51-77.
Dua, H. S., et al. (2000). Limbal stem cell deficiency: concept, aetiology, clinical presentation, diagnosis and management Indian J Ophthalmol 48(2) 83-92.
Fini ME, et al. (1998) Proteolytic mechanisms in corneal ulceration and repair. Arch Dermatol Res 290: S12-23.
Guo M, et al. (1989) Basement membrane and human epidermal differentiation in vitro. J Invest Dermatol 93: 372-378.
Herrick SE, et al. (2007) the potential of mesothelial cells in tissue engineering and regenerative medicine applications int J Artif Organs Jun;30(6):527-40.
Herrick SE, Mutsaers SE. (2004) Mesothelial progenitor cells and their potential in tissue engineering. Int J Biochem Cell Biol 36:621-42. Cross Ref Medline Web of Science.

(Continued)

*Primary Examiner* — David H Willse
*Assistant Examiner* — Javier G Blanco

(57) ABSTRACT

A new method for the treatment of ocular disease and injury is provided. The method involves the administration of a biocompatible implant, the porcine small intestinal serosa (or serous membrane), as graft/patch directly to the eye, for inducing restoration, remodeling, and repair of a tissue in a variety of injuries or conditions in the cornea, conjunctiva, and/or the eyelid due to trauma, diseases, or surgery. A focus on product interactions, safety profile has been fully defined and the membrane is reasonable in process, easy and convenient to prepare and significant in therapeutic effect. A simple standardized and straightforward method has been developed to fabricate this ultra-thin, delicate, and transparent material. Derived from well-defined mechanical strength, the serous membrane demonstrates consistency and flexibility that provides agile solutions for the physician.

3 Claims, No Drawings

(56) References Cited

OTHER PUBLICATIONS

Huang AJW, Tseng SC. (1991) Corneal epithelial wound healing in the abscense of limbal epithelium. Invest Ophthalmol Vis Sci 32: 96-105.
Inoue S, et al. (1983) Ultrastructure of Reichert's membrane, a multilayered basement membrane in the parietal wall of the rat yolk sac. J Cell Biol 97: 1524-1537.
Kefalides NA, et al (1979) Biochemistry and metabolism of basement membranes. Int Rev Cytol 61: 169-228.
Khodadoust AA, et al. (1968) Adhesion of regenerating corneal epithelim. The role of basement membrane. Am J Ophthalmol 65: 339-348.
Lavery FS. (1946) Lime burn of conjunctiva and cornea treated with amnioplastin graft. Transactions of the Ophthalmological Society of the United Kingdom 66:668.
Madri JA et al. (1984). The ultrastructural organization and architecture of basement membranes. In; Basement membranes and cell movement. CIBA Found symp 108 1984; 6-24.
Martinez-Hernandez A, Amenta PS. (1983) the basement membrane in pathology. Lab Invest 48: 656-677.
Timpl R. (1989) Structure and biological activity of basement membrane proteins. Eur J Biochem 180-487-502. 9.
Mutsaers SE, et al. (1997) Mechanisms of tissue repair. From wound healing to fibrosis. Int J. Biochem. Cell Biol. 29: 5-17.
Mutsaers SE. (2002) Mesothelial cells: their structure, function and role in serosal repair. Respirology 7: 171-91.
Mutsaers SE. (2004) The mesothelial cell. Int J Biochem Cell Biol. Jan;36(1):9-16.
Oh, J. Y., et al. (2008). The anti-inflammatory and anti-angiogenic role of mesenchymal stem cells in corneal wound healing following chemical injury. Stem Cells 26(4) 1047-1055.
Panda A, Nainiwal SK, Sudan R (2002) Failure of amniotic membrane transplantation in the treatment of acute ocular burns. Br J Ophthalmol. 86:831.
Peris-Martìnez C, et al. (2001) Multilayer amniotic transplantation in severe ocular graft versus host disease. Eur J Ophthalmol. 11: 183-186.
Recancof Garcia A (2001) Preparaciòn, preservaciòn y use de membrane amniòtica. Reemplazo conjuntival en Conejos. Tèsis de Graduaciòn. Universidad Francisco Marroquin, Facultad de Medicina. Dec. 2001. http://www.tesis.ufm.edu.gt/med/68124/tesis.htm.
Shafto C (1950) A simple method of inserting amniotic membrane grafts into the conjunctival sac. Br J Ophthalmol 34:445-446.
Steadman, M (2006). "The Goldbeater, the Cow and the Airship". Post & Tele Museum, Denmark. http://www.pttmuseum. dk/en/online_magazine/previous_articles/broadcasting/?id=74. Retrieved Sep. 12, 2009.).
Talmi YP, Finkelstein Y, Zohar Y (1990). Use of human amniotic membrane as a biologic dressing. European Journal of Plastic Surgery 13:160-162.
Thoft, R. A. and J. Friend (1983). The X, Y, Z hypothesis of corneal epithelial maintenance. Invest Ophthalmol Vis Sci 24(10) 1442-1443.
Tseng S, et al (2004) How does amniotic membrane work? Ocul. Surf. 2:177-187.
Tseng SCG, et al. (1997) Important concepts for treating ocular surface and tear disorders. Am J Ophthalmol 124: 825-835.
Vracko R. (1974) Basal lamina scaffold-anatomy and significance for maintenance of orderly tissue structure. Am J Pathol. 77: 314-346.
Weber L. Krieg T. Timpl R. (1964) Basal membranen: Struktur, Funktion, Pathologie. Hautarzt 35; 279-286.
Whitaker D, et al. (1982) The mesothelium and its reactions: A review. Grit Rev. Toxicol. 10: 81-144.
Yao, L., et al. (2012). Role of mesenchymal stem cells on cornea wound healing induced by acute alkali burn. PLoS One 7(2) e30842.
Ye 2006 Ye J, Yao K, Kim JC. (2006) Mesenchymal stem cell transplantation in a rabbit corneal alkali burn model: engraftment and involvement in wound healing. Eye 20(4):482-90.
Yiu S, Thomas P, Nguyen P (2007) Ocular surface reconstruction: recent advances and future outlook. Curr Opin Ophthalmol 18:509-514.
Yung S, Chan TM. (2007) Mesothelial cells for use in corneal injuries. Pent Dial Int. Jun;27 Suppl 2: S110-5. Mesothelial cells.
Zhou SY, et al. (2004) [A clinical study of amniotic membrane transplantation for severe eye burns at the acute stage]. Zhonghua Yan Ke Za Zhi 40:97-100.

* cited by examiner

SEROUS MEMBRANE FOR OCULAR SURFACE DISORDERS

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

REFERENCE TO A "SEQUENCE LISTING

Not Applicable

STATEMENT REGARDING PRIOR DISCLOSURES BY THE INVENTOR OR A JOINT INVENTOR

Not Applicable

FIELD OF THE INVENTION

This invention, in the field of ophthalmology, relates to a novel clinical application in ocular surface disorders of the porcine small intestinal serosa (or serous membrane), prepared with new processes.

BACKGROUND AND SUMMARY OF THE INVENTION

In the field of ophthalmology, the regeneration of a healthy ocular surface epithelium after traumatic injury or reconstruction techniques is one of the most difficult challenges for repair, and sometimes arise structural changes (vascularization and scarring, epithelial erosions or ulcerations occur among others) and/or functional (corneal opacity or lack of transparency) of undesirable consequences (Maldonado, 1995).

Regardless of origin, tissue damage is accompanied by complex systems of reparation for a high level of organization and differentiation, whose mechanisms are activated immediately after the aggression for proper restoration of the structures (Huang, 1991).

The healing consists of multiple processes, including migration of adjacent cells, mitosis (Kuwara, 1976), cell proliferation and differentiation and rearrangement structures of adhesion of extracellular matrix (Kaufman, 2009).

When the healing process fails to regenerate normal tissue transparency, is produced an opaque scar tissue, and depending on the severity of the case, can lead to visual defects (Rojas, 2009).

With the intraocular application of certain products, it is intended that the healing is complete with stable epithelium, minimal scarring, and prevent conjunctivalization and neovascularization (EMA, 2013).

Corneal epithelium integrity plays a pivotal role in maintaining health ocular surface (Tseng et al., 1997). Clinical conditions associated with epithelial defects and persistent and progressive corneal ulcers include "viral infections, autoimmune and endocrine diseases, thermal and chemical burns, and multiple ocular surgeries", according to Emiliano Ghinelli in US patent 20080108045.

Healing of the corneal epithelium is compromised by several ocular surgical procedures and is associated with numerous disease states. Delays in the reconstitution of the corneal epithelium, may result in permanent structural and functional perturbations with undesirable consequences (Maldonado, 1995).

According to Claes H. Dohlman "The corneal epithelium fulfills important functions since its absence or disease can lead to serious consequences. In the presence of a long-standing epithelial defect, the stromal surface dries easily and becomes irregular, the stroma swell, and clouds, ulceration and scarring may follow, and the entire eye becomes vulnerable to infection.

In the healed stage, the epithelium may have developed surface irregularities and reduced transparency. Such residual damage of the epithelium, resulting from acute or chronic disease or injury, is responsible for reduction of vision in an enormous number of people the world over." (Dohlman, 1971).

Good vision contributes greatly to a person's ability to interact with and function in his or her environment. Diseases of and injuries to the eyes can be severely debilitating and occur in a wide variety of forms.

In the treatment of various pathologies of the ocular surface have been used with varying success, the following: Amniotic membrane transplantation (Koizumi 2000) Autologous transplantation of nasal mucosa (Kuckelkom 1994), oral mucosa (Shore 1992), Tenon orbital (Teping 1989), artificial epithelium (Reim 1990) conjunctival transplantation (Thoft 1979) and treatment with autologous serum among others (Geerling 2004; Kojina 2005).

Particularly the amniotic membrane has been used to solve various problems of the ocular surface in at least 20 ophthalmic procedures, including persistent corneal epithelial defects, pterygium surgery, and conjunctival defects after removal of superficial tumors, acute and chronic chemical injuries, Steven Johnson syndrome, and in the treatment of ocular cicatricial pemphigoid among others (Sangwan 2007).

The amniotic membrane and chorion has been used in surgeries, documented as early as 1910 with the use by Davis on burned and ulcerated skin (Davis 1910)

The isolated amnion alone was first used by Brindeau in 1935 and Burger in 1937 as a graft in forming artificial vaginas. Between 1941 and 1948, Kubanyi used "live" amnion in patients with burns, traumatic skin wounds, and enterocutaneous fistula secondary to surgery for lysis of adhesions. The isolated amnion, with preservation in a technique termed "amnioplastin", was first reported by Chao and associates in 1940. Chao used amnioplastin for continual dural repair, peripheral nerve injuries, conjunctival graft and flexor and tendon repair. In the Russian literature, this technique was also used for fresh trauma by Pikin in 1942.

In ophthalmology, the use of an amniotic membrane was first reported by De Rotth in 1940 for treatment of conjunctival tissue loss (De Rotth A., Arch. Ophthalmol., 23:525-5 (1940)). In 1993, Batle and Perdomo reintroduced the use of an amniotic membrane as a conjunctival substitute (Batle J F, Perdomo F J, Ophthalmol., 100:107 (1993).

Kim and Tseng then showed in 1995 that an amniotic membrane facilitated corneal surface reconstruction in rabbits after epithelial removal and limbal lamella keratectomy and introduce a method of preservation and storage of this material (Kim J C and Tseng S C, *Cornea*, 14:473-84 (1995)).

Presently, the amniotic membrane has been recognized as an excellent material for the treatment of certain ocular disorders such as persistent corneal epithelial defects with ulceration, pterygium and for conjunctival surface reconstruction (Baradaran 2007).

It is noteworthy that the amniotic membrane has a thick basement membrane, which in the likeness of ocular tissues, and indicate that this material can replace conjunctival basement membrane and promote epithelialization (Fukuda 1999).

International patent application number PCTVUS2003/029390 from Ghinelli describes the use of a human amniotic membrane for prophylaxis and treatment of diseases and conditions of the eye and skin.

Several methods for the preparation of amniotic membranes for surgery have been described. These include alcohol dehydration, preservation in antibiotics in saline, either with or without separation of the amniotic and chorionic layers (Dua 1999).

Other methods have been disclosed more recently. For example, Tseng (U.S. Pat. Nos. 6,152,142 and 6,326,019B1) discloses a method relying on freezing for preservation of the amniotic membrane; Hariri et al, (US Patent 20040048796) disclose a method designed to decellularise the amniotic membrane leaving it devoid of all but a collagenous membrane.

The use of amniotic membrane as a technique of choice in certain pathologies of the ocular surface with conjunctival involvement (pterygium, especially primary, symblepharon and sinequiantes processes with restricted ocular motility), found a higher recurrence of pathology prior and more aggressively after transplantation of said material (Lopez, 2012).

Unfortunately, an improvement in the patient's visual outcome following application of amniotic membrane tissue is often unsuccessful (Solomon et al., 2002). U.S. Pat. No. 7,494,802 by Scheffer observed an early dissolution of the AmnioGraft™, i.e., shorter than one week in human patients with an exposure problem.

And Dua, in his patents US20080193554, and WO2007010305A3 detected inconsistencies in the clinical outcome following the use of amniotic membrane and refer: "in the treatment of certain conditions have been observed within the inventors' clinical practice, including excessive scarring in severe conjunctival wounds".

In preparing competitive products, after the human extraction of the raw material, sophisticated laboratory equipment and manufacturing expertise is needed (for example, Engineers and personnel for the assembly and processing) before obtaining the final product.

The main limitation of these products is their expense: high price in order to compensate the high investment cost.

There is an ongoing need for alternative therapies for the treatment of ocular diseases and injuries, particularly low-cost therapies that are readily accessible and easy to use.

It should be noted that in the process for the purification and isolation of the tunica serosa from the small intestine of porcine tissue (or serous membrane), which comply with all rules and regulations, the sophisticated processes of competitor are simplified, with lower costs and less human skill to prepare the final product.

The serous membrane of the present invention is abundant, inexpensive and the methods to process provide effortlessness to manufacture while the competitors require high degrees of synthesis which drive up costs.

Constituents of the Fine Structure of the Intestinal Serosa

The microscopic observation shows that a three-layered serous membrane (the Latin anatomical name is tunica serosa) is structurally composed of one layer of squamous epithelial cells (simple squamous epithelium), known as mesothelium, which face the peritoneal cavity, which rests on a basement membrane (basal lamina) and a deeper layer of loose connective tissue (Janik, 1982; Whitaker, 1982; Eroschenko, 2008; Van der Flier, 2009).

For purposes of the patent, it is necessary to do a more extensive description of two of these structures: the mesothelium and the basement membrane, and past use of the Golbeater's Skin.

The Mesothelium

The epithelial layer, known as mesothelium (that covers the external surfaces of the digestive organs, lungs, and heart), consists of a single layer of avascular flat nucleated cells (simple squamous epithelium) which produce the lubricating serous fluid. These cells are bound tightly to the underlying connective tissue (Eroschenko, 2008).

The mesothelium is composed of an extensive monolayer of specialized cells (mesothelial cells) that line the body's serous cavities and internal organs (Eroschenko, 2008). Morphological studies of the mesothelium of several mammalian species, including rat, mouse, dog, hamster, rabbit, horse and humans have shown, with minor exceptions, which are essentially similar irrespective of species or anatomical site. (Whitaker, 1982; Odor, 1954).

The main purpose of these cells is to produce a lubricating fluid that is released between layers, providing a slippery, non-adhesive, and protective surface (Van der Flier, 2009).

With the gradual accumulation of information over the years, the mesothelium is now recognized as a dynamic cellular membrane with many important functions (Mutsaers, 2002).

These include transport and movement of fluid and particulate matter across the serosal cavities, leucocyte migration in response to inflammatory mediators, synthesis of pro-inflammatory cytokines, growth factors and extracellular matrix proteins to aid in serosal repair, release of factors to promote both the deposition and clearance of fibrin, antigen presentation, immune surveillance, and regulation of inflammatory processes and wound healing (Mutsaers, 2002).

The Basement Membrane

The basement membrane is a specialized extracellular matrix compartment, which participates dynamic and active in important roles in cell differentiation, tissue architecture and repair mechanisms (Martinez, 1983; Weber, 1964).

It is recognized that the intact basement membrane is vital to the control of normal growth and epithelial differentiation (Stoker, 1990) and pre-existing components are required to promote the reconstruction of the basement membrane (Andriani, 2003; Herrick, 2007).

Typical, "common" basement membranes are usually described as being composed of three layers (Kefalides et al., 1979).

The dense sheet, the lamina *lucida*, and fibroreticular sheet, which basement membrane attached to the underlying connective tissue (Kefalides, 1979; Vracko, 1974; Madri, 1984, Inoue, 1983).

The lamina densa, the main layer of the basement membrane, is separated from the surface of adjacent cells by a lucent layer or space, the lamina *lucida*, while the third layer, the lamina (or pars) fibrorecticularis, forms a transitional zone between the lamina *densa* and connective tissue (Mutsaers, 2002; Dohlman, 1971).

Basement membranes are extracellular sheet-like layers, no wider than 200 nm, which separate certain tissues including epithelia, endothelia, muscle fibers, and the nervous system, from connective tissue compartments (Kefalides et al., 1979; Inoue, 1989).

Basement membrane of the corneal epithelium is not in any way unique—most epithelia of the body have a similar structure—but it may be of critical importance to the adhesion of the corneal epithelium in a way not quite understood (Goldman, 1969).

If the basement membrane is surgically removed, the development of epithelial adhesion is much slower (Goldman, 1969). Long-standing epithelial defects and recurrent erosion in the eyes of patients may be explained by damage to the basement membrane (Goldman, 1969).

Eventually, however, the epithelium secretes new basement membrane and becomes well attached again to the rest of the cornea (Dohlman, 1971). Basement membrane that provides support to the corneal epithelium is important in maintaining cell polarity and in wound healing processes (Maldonado, 1995).

Taking advantage of its basement membrane content, in a similar way to the amniotic membrane, the new serous membrane (or serosa) has in its constitution a basal membrane, as preexisting component can accelerate the reconstruction of the ocular structure.

Golbeater's Skin

Golbeater's Skin or intestinal serous membrane has a long history. The Ebers Papyrus compiled around 3750 B.C. describes Egyptian surgeons using dried intestine for suturing wounds. And the gold leaf that adorns ancient sarcophagi was made with "goldbeater's skin," the incredibly thin but strong outer membrane of calf intestine (Schwarcz, 2013).

Egyptian craftsmen managed to produce gold leaf that was an almost unimaginable 0.000125 millimetres thick and separating the layers with "goldbeater's skin" was critical to prevent the leaves from fusing together (Schwarcz, 2013).

Antoine Germain Labarraque, solved the problem of stench in the "boyauderies," the factories where animal guts were turned into strings for musical instruments, sutures and "goldbeater's skin" (Schwarcz, 2013).

Joseph Thomas Clover in 1862 invented an apparatus for the inhalation of chloroform "Clover portable regulating ether inhaler". This consisted of a large reservoir bag lined with goldbeater's skin. (Sykes, 1960).

U.S. Pat. No. 174,465 was issued to Alexander Graham Bell in 1876, which used to build your stretched diaphragm or drum with goldbeater's skin.

It has also been reported using when repairing holes and tears of damaged parchment manuscripts. " . . . on Sep. 30, 1898, at the second meeting of the Society Bibliographica Italiana in Turin, report from Franz Ehrle, s.j., . . . spoke . . . about the severe degradation of paper . . . and the need to find ways to staunch the massive destruction that threatens millions of items and the discussion turned to the use of Goldbeater's skin" (Ehrle, 1909).

U.S. Pat. No. 552,612 in Jan. 7, 1896 was issued to Warren Herbert Frost for the construction of their musical instrument "Zobo" by diaphragm made from goldbeater's skin.

Around 1912 the Germans adopted the material for the internal gas bags of the "Zeppelin" and then used in the USS Shenandoah. (Steadman, 2006).

To date, other industrial application of these sheets can be used to make clarinet, piccolo, or flute pads or in the Talas Online catalogue used for repairing parchment and vellum.

U.S. Pat. No. 3,562,920 entitled "Tubular sheet and strip form prostheses on a basis of biological tissue" in Feb. 16, 1971 Berhard Braun use the Goldbeater' skin in his construct.

The 920 Braun Patent comprising a plurality of structural elements to form prosthesis that work together, viewed from the perspective to accomplish the intended use, and must be considered that the individual components not perform the same function derived is needed structural combination to achieve that goal.

Braun uses his discovery to produce prostheses capable "for use as vascular, esophagus, bronchus, intestinal, ureter and cardiac valve prostheses and as other corrective part of various organs such as liver", "as used for prosthetic repair of the cystic duct, the ureter, the esophagus or, in special cases, blood vessels". "to close defect in the tympanic membrane and the heart wall, for hollow-walled organs or as heart valves . . . are also used to repair damage to parenchymatous soft tissue, for example, in the liver, kidney, spleen and pancreas." which is achieved by means of invasive techniques (make cuts in the skin which cause damage to tissue, nerves, and blood vessels) and fixation with sutures, whose use is totally different from the intended use of the graft of the present application.

The U.S. patents: A. U.S. Pat. No. 3,562,920; B. U.S. Pat. No. 5,755,791; and C. PGPUB 2005/0202058 show several common elements: change natural resources (raw materials) for the construction of a finished product with variable layers in sequence, so that the final product is treated as a single unit for interoperability.

When changes are made any change affects the entire model and affecting their attributes. The preparation of the products in this "complex" technology "requires the existence of a rigid structure (hard materials) to ensure the stability of the final product to carry out the proposed function.

In U.S. patent 2005/0202058 by the inventor Michael C. Hiles, the text is not clear, and careful analysis shows that the submucosa plane (site from which 058 patent obtain the extracellular matrix materials) can never include the serous layer in its constitution, because the submucosal plane in the anatomy and histology of the digestive organs lies one level below the serous layer with different structure, cellular composition and bioactive components.

It should be noted a considerable difference between the manner of use of the prosthesis or graft in Patents 920, 791 and 058 and the use the graft of the applicant.

The patents 920, 791 and 058, refer than the graft being placed over vital structures such as vessels (vascular patches), viscera's (esophagus, bronchus, intestinal), or even heart or lung, and also used to repair damage to parenchymatous soft tissue, for example, in the liver, kidney, spleen and pancreas.

To apply the prosthesis or graft of Patents 920, 791 and 058, invasive procedures are required that make cuts in the skin. Tissues, nerves and blood vessels are damaged during these procedures.

By contrast, the procedure of the applicant is a non-invasive technique that does not damage the tissues, and not penetrate the eyes at the site of implantation, that pursues restoring this vital structure. The intended use of the graft in this invention is directed for tissue regeneration and repair damaged ocular surfaces at the site of implantation.

Golbeater's Skin has a long history of use according to the description was described in previous lines and includes use of the product of bovine origin sold in Talas Online catalogue.

Prior experience with this product by the author, to compare materials from the intestines of cattle and pigs the applicant describes the complications associated with the use of this product of bovine origin to be implanted in the wound site, which include rigidity, and higher disadvantage by the damage to the fragile, newly formed epithelium, thus extending healing times, prolong the duration of hospital stays and demand additional therapeutic interventions.

In the Design Control Guidance for Medical Device Manufacturers the U.S. Food and Drug Administration establishes the following Requirements*: "§ 820.3 (s) Quality means the totality of features and characteristics that bear on the ability of a device to satisfy fitness-for-use, including safety and performance (Design Control Guidance for Medical Device Manufacturers 1997)

§ 820.30(f) Design verification. Each manufacturer shall establish and maintain procedures for verifying the device design. Design verification shall confirm that the design output meets the design input requirements. The results of the design verification, including identification of the design, method(s), the date, and the individual(s) performing the verification, shall be documented in the Design History File.

§ 820.3(y) Specification means any requirement with which a product, process, service, or other activity must conform.

§ 820.3(z) Validation means confirmation by examination and provision of objective evidence that the requirements for a specific intended use can be consistently fulfilled. Verification means confirmation by examination and provision of objective evidence that specified requirements have been fulfilled."*

*(http://www.fda.gov/MedicalDevices/DeviceRegulationandGuidance/PostmarketRequirements/QualitySystemsRegulations/§ 820.3(aa)

The objective of design controls is to ensure adequate oversight by making verification activities explicit and measuring the thoroughness of their execution.

Following are a few examples of verification methods and activities recommended in Design Control Guidance for Medical Device Manufacturers from the US Food and Drug Administration: 1. Failure modes and effects analysis. 2. Package integrity tests. 3. Biocompatibility testing of materials. 4. Bioburden testing of products to be sterilized, which are not followed in any of the preparation processes of the product of bovine origin sold in Talas Online catalogue.

As with any new product, the introduction into clinical use need adequate controlled study, issues involving side effects and the efficacy in the clinical experience.

This can lead to unanswered questions regarding appropriate use and indications of the Golbeater's Skin material from Tales online catalogue.

The applicant aware that the above information may be used to conduct a risk-based assessment before any decision is taken about the use in Goldbeater's skin product for ocular surface lesions and it is not considered that the product meets neither requirement.

Overall, the medical need to replacing the deficient stromal connective tissue as well as stimulating re-epithelialization in the injured ocular surface, has not been met.

As described above, according to the present invention, with the use of serous membrane of the present invention set forth in the examples, it is possible to improve the deficient stromal connective tissue as well as stimulating re-epithelialization in the injured ocular surface, and higher therapeutic effects can be expected.

From a social perspective the product is accessible, reasonably, for the benefit of the population who are economically disadvantaged and, in the future, may need it.

For developing countries, take into account concerns of "access" to technology. The present invention addresses this need.

In summary: technology improves the lives of hundreds of thousands of patients and solves a major problem for the less developed areas of the world by providing an economic product.

BRIEF SUMMARY OF THE INVENTION

The present invention relates to a new biological and biocompatible tissue graft, appropriately procured and processed, a lyophilized porcine small intestinal serosa (or serous membrane), wherein the tissue comprises a three-layered structure, which may be used either as a 'substrate' to replace the damaged ocular tissue or as a 'patch' (biological dressing), or a combination of both, for reconstructing damaged ocular surfaces and to promote healing in a variety of injuries or conditions in the cornea, the conjunctiva, and/or the eyelid tissues after injury due to trauma, diseases, or surgery, in which the graft does not elicit immunological reactions.

BRIEF DESCRIPTION OF THE SEVERAL VIEWS OF THE DRAWING

Not Applicable

DETAILED DESCRIPTION OF THE INVENTION

Description of the Preferred Embodiments of the Invention

A description of preferred embodiments of the invention follows. It will be understood that the embodiments of the invention are shown by way of illustration and not as limitations of the invention. At the outset, the invention is described in its broadest overall aspects, with a more detailed description following. The features and other details of the compositions and methods of the invention will be further pointed out in the claims.

It is also to be understood that the terminology used herein is for describing particular embodiments only, and is not intended to be limiting, since the scope of the present invention will be limited only by the appended claims.

Membrane, as the term is used herein, is a biological membrane that comprises a simple squamous epithelium, a thin basement membrane (basal lamina) and submesothelial connective tissue layers from the the tunica serosa from the small intestine of pig.

In other embodiment the membrane is a tissue covering. As used herein, the terms "tissue covering," "covering for ocular surface," and "covering" have the same meaning and include, for example, a dressing, a covering to protect tissue or to prevent adhesions, or to promote healing or growth of tissues.

As used herein, the term "subject" is used to mean any animal, preferably a mammal, including a human or non-human subject such as livestock (e.g., horses, cattle, and the like), domesticated animals (e.g., dogs, cats, and the like). The terms patient, subject, and individual are used interchangeably.

The term "treat," "treating" or "treatment" as assumed herein relates to combat the effects caused because of the disease or condition of concern in a subject.

The terms "transplant," "transplanting," "transplanted" or "transplantation" are used interchangeably herein with the terms "implant," "implanting," "implanted," "implantation," "graft," "grafted," or "grafting."

In general, a membrane suitable for use in an embodiment comprise a biocompatible material. "Biocompatible," as the word is used herein, refers to a material that has no medically undesirable noxious or unfavorable effects on biological function.

In some embodiments of the invention, the tunica serosa (or serous membrane) that is used is porcine. However, those of skill in the art will recognize that the tunica serosa (or serous membrane) from other mammalian species may also be successfully utilized, examples of which include but are not limited to horse, rabbit, lamb, cow, sheep, primates, etc.).

Means selected "ocular surface" any list structure comprising: epithelia of the cornea, limbal-corneal or conjunctival tear film overlying or underlying stroma to these structures.

The novel features which are believed to be specific to the invention, will be better understood from the following description of preferred embodiments.

The invention relates, in one embodiment, to provide defined processes for the use of a membrane suitable for ocular surgical procedures.

The invention relates, in another embodiment, for the human or veterinary use of novel serous membrane graft for reconstructing damaged ocular surfaces and to promote healing in a variety of injuries or disorders involving the cornea, the conjunctiva, and/or the eyelid after injury due to trauma, disease, or surgery.

In a specific embodiment, the present disclosure is directed to a new and effective method of repairing a disorder or injury in an eye, in a variety of ophthalmic indications, with transparent biocompatible implant, the porcine small intestinal serosa (or serous membrane).

In one embodiment the serous membrane is preferably administered to a subject for repairing, reconstructing, replacing, or supplementing a recipient's damaged, compromised, or missing ocular tissues.

In another embodiment the serous membrane of the present disclosure can be used to treat any subject in need of treatment, including but not limited to humans, primates, and domestic, farm, pet, or sports animals, such as dogs, horses, cats, sheep, pigs, cattle, rats, mice, and the like.

In a specific embodiment, relates to a membrane for implantation in space of an eye, for human or veterinary use, as overlay graft (to facilitate epithelialization), inlay graft (to replacing the deficient stromal connective tissue as well as stimulating re-epithelialization) or combined inlay+overlay grafts (to promote and protect epithelial recovery)

In another embodiment, the purified membrane described herein can be used in several indications, either as a 'substrate' to replace the damaged ocular tissue or as a 'patch' (biological dressing), or a combination of both for repairing, reconstructing, replacing, or supplementing a recipient's damaged, compromised, or missing ocular tissue.

In a specific embodiment, surgery or other procedures are performed to correct, repair or ameliorate injuries to the eye. Generally, the surgery or other procedure comprises contacting the site of trauma with one or more pieces of biomaterial from the tunica serosa from the small intestine of porcine tissue (or serous membrane). The biomaterial can be held in place by, e.g. sutures or a tissue adhesive suitable for use in the eye.

Continuing the embodiment, the serous membrane can be administered by any suitable technique like for any grafts, and it is important that the graft site is properly prepared by removing loose epithelium and necrotic ocular tissues.

Serous membrane covering for a tissue surface according to an embodiment of the invention can be placed on a target tissue for therapeutic treatment of the ocular region.

In one embodiment, one layer of membrane generally is sufficient, except for deep ulcers. In another embodiment it is also feasible to use two or more layers of serous membrane to fill the defect if necessary.

In another embodiment, the multi-layered implantation material can be cut to appropriate dimensions for a application to form a multi-layered implant.

In one embodiment, the tissue it is cut and of a size and shape that is desired for the applicable surgical procedure in which the tissue will be used, and if preferred, can be applied surgically to the desired site by use of surgical sutures or tissue adhesives, to reduce premature graft retraction and to allow quick graft adherence to the defect site.

In some embodiments, the tissue product does not require an orientation relative to the substrate (i.e. any side of the serous membrane may be in contact with the substrate).

The covering according to an embodiment can remain in place on the damaged tissue surface for a sufficient period of time to bring about a noticeable improvement in the condition of the tissue occurs.

The invention relates, in another embodiment, to provide defined new processes to produce a membrane suitable for direct surgical use.

A detailed look at the history and procedure for harvesting and using serous membrane for surgical procedures and processes for their mode of treatment of the material are established in the past in the disclosure of invention of the patent submitted by the applicant: Application WO/2009/040768, Number: IB2008/053921 Publication Date: Apr. 2, 2009 and U.S. Pat. No. 9,023,342 B2 Publication Date: May 5, 2015 which is incorporated herein by reference in its entirety.

In a specific embodiment, only materials from proper suppliers that ensure full traceability should be used. In another embodiment the Serous Membrane Graft is obtained from animals that have passed ante mortem and post mortem inspection and meet regulatory requirements under U.S. federal inspection (USDA-FDA).

In another embodiment manufacturer provide a certificate of compliance for every lot of materials, about the quality of tissues removed and their appropriate handling after removal from the animal.

In one embodiment the steps for the preparation of the material are the following sequences, which in this Detailed Description are described concisely and more detailed explanations and discussion regarding each individual step will follow extended in the example number one of the present patent of invention.

In a specific embodiment, the animal is slaughter and remove the small intestine. In another embodiment this is stored refrigerated or on wet ice in sealed container. Continuing the embodiment, the material must then be cleaned and separate the mesentery fat from the small intestine and keep the intestine. In another embodiment the tract is squeezing to force out the mucosal contents and gently run water inside the mucosal surface of the tract, until the inner surface of the tract is clean, to remove any food waste and feces.

In another aspect of the invention, the mucosal tract is cut longitudinally to produce a single flat membrane. Continuing the embodiment, the serosa in then separated from all other tissues that make up the small intestine. In a specific embodiment, the muscularis propia, the sub mucosa, and mucosa is delaminated from this surface by gentle abrasion manually and/or using moistened gauze and discarded. In another embodiment the tissue is cut into smaller sections approximately 20 cm.

In one embodiment the serosa tissue is now placed in n-alkyl (50% c14, 40% c12, 5% c16) dimethyl benzyl ammonium chloride for minimum of 6 hours at room temperature (or at 4 C in cooler overnight) or in another embodiment an alternative method involves immersing the tissue source (e. g. by submersing) in 0.1% (v/v) peracetic acid (PAA) and 95.9% (v/v) sterile water for two hours.

Continuing the embodiment following the disinfectant soak, the serosa is rinse three times for at least 5 minutes, using distilled water. In another embodiment for sublimation drying (lyophilization) the serosa tissue is place in the lyophilizing trays in single layer and follow preset lyophilizing program until moisture is removed and desired drying is achieved.

In an embodiment, the amniotic membrane includes a plurality of holes with a perforation across the entire piece of membrane. Preferably, the biomaterial used in the methods of the invention is stored in a sterile double peel-pouch package.

In another aspect of the invention, sterilization be accomplished using gas, e.g., ethylene dioxide, and is preferably done using radiation, for example, gamma radiation, or electron beam irradiation using methods known to one skilled in the art. In some embodiments, a tissue product described herein is stored for later use.

While the compositions and methods of this invention have been described in terms of preferred embodiments, it will be apparent to those of skill in the art that variations may be applied to the methods and in the steps or in the sequence of steps of the methods described herein without departing from the concept, spirit and scope of the invention.

The following examples are included to demonstrate preferred embodiments of the disclosure. It should be appreciated by those of skill in the art that the techniques disclosed in the examples which follow represent techniques discovered by the inventor to function well in the practice of the invention, and thus can be considered to constitute preferred modes for its practice.

However, those of skill in the art should, considering the present disclosure, appreciate that many changes can be made in the specific embodiments which are disclosed and still obtain a like or similar result without departing from the spirit and scope of the invention.

While the fundamental novel features of the tissue disclosed herein have been described, it will be understood that various omissions, substitutions and changes in the form and details may be possible without departing from the spirit of the present disclosure.

Example #1

Product Manufacturing Methods

A simple standardized and straightforward method it has been developed to fabricate the tunica serosa of the small intestine of the pig.

In the facilities of the company that prepares materials of swine origin, the pig receives ante and post-mortem inspections by the USDA and acceptance with the FDA in accordance with ISO 22442-2:2007 Medical devices utilizing animal tissues and their derivatives—Part 1: Application of risk management Part 2: Controls on sourcing, collection and handling.

Regulations to the Control of raw materials in the U.S. Code of Federal Regulations (CFR), ICH, and other regulations/guidance's cited below: Regarding 21 CFR 211.110 Control of in-process materials, ICH Q5A/D for cell substrates and viral safety, ICH Q7 discussing the need to check with appropriate materials specifications, ICH Q10 stating that a bio manufacturer is responsible for the quality of purchased materials.

In summary this company meets the following important aspects: adherence to regulations, quality systems emphasis, quality management, monitor/audit of the manufacturing process, aseptic techniques required during production, purity product and process-related impurities, maintenance of equipment, batch production and control records and maintenance of documentation.

Initial Tissue Collection, Material Check-In and Evaluation

A detailed look at the history and procedure for harvesting and using serous membrane for surgical procedures and processes for their mode of treatment of the material are established in the past in the disclosure of invention of the patent submitted by the applicant: Application WO/2009/040768, Number: IB32008/053921 Publication Date: Apr. 2, 2009 and USPTO Patent Application Number: US20100135964 Publication Date: Jun. 3, 2010 which is incorporated herein by reference in its entirety.

More detailed descriptions to obtain the fine structure of porcine tunica serosa regarding each individual step will follow.

In general, the method for preparing the serosa comprises the steps of obtain freshly harvested small intestine of warm-blooded vertebrate, preferably porcine origin, from proper suppliers that ensure full traceability.

In all processes the standards to be met is done following Good Tissue Practices (GTP) to ensure that no contaminants are introduced into the tissue products.

It should be emphasized that in these processes, the equipment and the facilities are cleaned and decontaminated according to conventional and industry-approved decontamination procedures and all major processing are documented following industry practice, and FDA-USDA regulations standards.

Initial Tissue Collection

At the site of animal sacrifice in the designated slaughter area the small intestine, with an average length of 15 to 20 meters, was carefully separated from the animal with appropriate gloves. This is primarily a hand and/or knife operation.

To separate from the body, it removes the viscera (the small intestine) of the animals that is collected in a large container. It proceeds to cut through the fat surrounding the offal and sever any tissue that connects to the abdominal cavity.

After harvest the viscera, should be inspected in relation to the smell (free of signs of putrefaction: no rancidity, no sour (acidic) smell), irregularity or abnormality in shape or color appearance (typical from white, to pink, to grey) and discard the material if any of them be present and only used the healthy small intestine.

Laboratory Working Areas

The laboratory should be kept neat, clean and free of materials that are not pertinent to the work. The surfaces of Stainless steel table should be decontaminated with freshly prepared hypochlorite solution at 1 g/1, before and after each use and application of pressure with vigorous scrubbing greatly improves the removal of grease and other unwanted contaminants from a preparation surface.

Gross Tissue Processing Transportation of Tissue Following Recovery

Care is then taken to remove blood clots and other extraneous tissue until the viscera are clean and ready for further processing. This step must be done with adequate care so as not to tear the tissues.

Stripping Out Intestinal Content

The material must then be cleaned, first by squeeze the tract to force out the mucosal contents.

Them the primary material is transfer to an area that allows copious amounts of circulating fresh water for cleaning its external and internal surfaces and mainly run water through the lumen of the intestine to remove any food waste and feces.

The tissue is washed repeatedly until the inner surface of the tract is clean. Any visible traces of contamination were removed by gently rubbing with fingertips and care is then taken to remove blood clots and other extraneous material until the membrane tissue are clean and ready for further processing.

Using a blunt instrument, or sterile gauze, any residual debris or contamination is also removed. This step must be done with adequate care, so as not to tear the tissues. Any areas of the viscera cleaned too aggressively and appear clear will be unacceptable and will ultimately be discarded.

Separation of the Small Intestines from Mesenteric Tissue

The material must then be prepared on a sanitized table for the separation from adhering mesenteric (connective and fatty) tissues from the small intestine and keep only the intestine. This step must be done with adequate care, so as not to tear the tissues.

In other step a visual inspection is performed. The tissue is examined for signs of damage. A determination is made, at this point, as to whether the tissue is acceptable and once all criteria are met, the small intestine is released for processing.

The viscera are then either shipped on wet or dry ice to the processing facility or it is temporarily stored refrigerated or on wet ice in sealed container until ready for further treating.

Process to Separate the Serosa

Gross processing and separation of the tissue layers then takes place, if the material is deemed acceptable for further processing.

The principle for optimal production is to start processing the viscera as soon as possible after slaughter because the intestines are easier to manipulate.

In one aspect, the process for preparing the serous layer and removing the inner layer, involves in a first process, by passing the intestine over a cylindrical tube, cut the material in the longitudinal axis, with a single cutting point on its surface to produce a single flat membrane using surgical instruments.

Next the serosa layer in then carefully separated from all other tissues that make up the small intestine. This is achieved by placing the tract on a flat surface.

The method according to the invention, involves carefully separation of the tissue layers, to detach the muscularis, tunica submucosa, and tunica mucosa in order to preserve intact the outer structure, the serosa, because they are the primary material of the present invention.

The separating step may be carried out, and the muscularis, sub mucosa, and mucosa is delaminated from the serosa by gentle abrasion, manually and/or using moistened gauze, and it can be discarded in an appropriate biohazard container.

At the time the serosa can be substantially delaminated, and after removal of the other layers, the serosa is ready to be used to produce the tissue graft. Each tissue graft is then given a final inspection to confirm that there are no tears or holes.

The serous membrane appears as a thin, simple, homogeneous, and perfectly transparent membrane.

Membrane suitable for use in an embodiment of the invention generally includes an epithelial layer, a basement membrane, and a stroma, and the combination of the three layers preferably having a total thickness about 0.5 mm.

The isolated serous layers in the form of continuous sheets of tissue are then further processed and cut into smaller sections of 20 cm.

Chemical Decontamination

The membrane tissue is then placed into a sterile container for the next step of chemical decontamination.

The chemical decontamination comprises contacting the serous membrane with a suitable chemical, such as n-alkyl (50% c14, 40% c12, 5% c16) dimethyl benzyl ammonium chloride or in another embodiment an alternative method involves immersing the tissue source (e. g. by submersing) in 0.1% (v/v) peracetic acid (PAA) and 95.9% (v/v) sterile water for two hours.

Initially the disinfectant is prepared as follows: in two containers, two gallons of distilled water and 2.5 milliliters of n-ALKYL (50% C14, 40% C12, 5% C16) DIMETHYL BENZYL AMMONIUM CHLORIDE are added in each container.

The serosa tissue is now placed in this pre-mixed disinfectant for minimum of 6 hours at room temperature (or at 4 C in cooler overnight).

Following the disinfectant soak, the tissue is gently removed from the container, slightly agitated to facilitate removal of the chemical solution and placed in a sterile basin containing normal saline solution, and further comprises the step of rinse the serosa tissue three times for 10 minutes, until chemical has been eliminated.

Next, the now-rinsed tissue is ready to be dehydrated immediately (i.e., within 30 minutes) after washing the tissue is ready to be dehydrated and processed further.

In the previous patent the excess water can be removed from the preparation by dehydration and in this invention is obtained and preserved in a new way.

An exemplary method of removing the water is by use of lyophilization by means of a commercially available lyophilizer or freeze-dryer technology, described in more detail in the following example.

The serous membrane is spread in single layers and placed on lyophilization processing trays and the product is lyophilized (i.e. freeze-dried) follow preset lyophilizing program.

When completed, the processed tissue graft has a semi-transparent appearance with a whitish coloration.

In some embodiments, the process of lyophilizing described herein does not destroy the natural structural integrity of the tissue product.

After the lyophilization phase, the serous membrane can include a plurality of aligned holes across the entire piece of the material, to produce a mesh-type configuration, using a laser drilling technique, a manual drilling technique, or by direct puncture.

Cutting & Packaging

Once the tissue has been adequately lyophilized, the tissue is then ready to be cut into specific product sizes and appropriately packages for storage and later surgical use.

The lyophilized sheets are sectioned into desired sizes (e.g. 2.5-3.0 cm.×2.0-2.5 cm, etc.) using any sharp cutting device (e.g. a scalpel, etc.).

After made the holes and cutting, each separate piece is placed into sterile/critical environment in an "inner" pouch and then packaged in an "outer" pouch for further protection, storage, and shipment.

This process is repeated for each separate graft and seal both "inner" and "outer" pouch using the heat sealer.

Packaging materials for use in packaging pharmaceutical products are well known to those of skill in the art and the pack can for example contain metal or plastic foil, such as a blister pack.

Preferably, the biomaterial used in the methods of the invention is stored in a sterile double peel-pouch package. In some embodiments, a tissue product described herein is stored for later use.

Sterilization

The lyophilized products are shipped to a contract sterilizer to terminal sterilization by any suitable medically acceptable method: for example, using gas, e.g., ethylene dioxide, exposed to gamma radiation at 17-30 kGy, or exposed to an electron beam for a period sufficient, to sterilize the tissue product.

This process pursues achieve a Sterility Assurance Level (SAL) sufficient to kill at least 99.9% of bacteria or other potentially contaminating organisms.

Final Inspection

Sterilized product returned from the contract sterilize company, is inspected for shipment and release to the end user. Inspection will include package integrity and final labeling inspection, to name a few.

This final inspection ensure that the product contained therein matches the product specifications and inspected to determine the existence of holes, broken seals, tears, contamination, or other physical defects.

Units passing inspection are released for storage, distribution and subsequent transplantation. Membranes were now considered transplant ready and stored at ambient temperature conditions.

Example #2

New Processes and Method to Modify Naturally-Occurring Product of Nature

Part this section of the recognition that the material is created wholly by nature unassisted by man, so that invention can be attributed only to the process and method to modify this natural physical structure and the method of using the same.

This application has been discovered useful processes (conceived in 1990) for the isolation of a product from the tunica serosa of the small intestine of pigs, characterized as an ultra-thin, delicate, soft, transparent, single layer material with markedly different characteristics of the structural-functional properties of the original.

Having completely abandoned the product obtained from the serosa of cattle, over twenty years ago, attention was focused on the pig intestinal serosa.

Processes for their mode of treatment of the material are established in the disclosure of invention of the patent granted to the applicant: Application WO/2009/040768, Number: IB2008/053921 Publication Date: Apr. 2, 2009 and U.S. Pat. No. 9,023,342 B2 Publication Date: May 5, 2015.

In which reads as follows, which has been copied literally: "Col. 1 lines [0004] [0005] "Disclosure of Invention: The tissue graft material is made from the tunica serosa of the small intestine of a warm-blooded vertebrate, which has been delaminated from the tunica muscularis, tunica submucosa, and the tunica mucosa of the intestinal tissue. The tissue graft material may be perforated by discrete punctures. The tissue graft material is dehydrated by air drying or vacuum drying, sterilized with ethylene oxide, and stored in a hermetically sealed enclosure at room temperature until needed, having an indefinite storage life."

New Processes in the Production of the Material

Current process be enhanced by the applicant. On this basis proceeded in accordance with the Good Manufacturing Practices (GMP) and the Quality Systems regulation (GMP's) established by FDA for manufacturing devices.

The new processes for producing porcine biological raw material with low risk, be made of a company that properly ensured origin of animal-derived raw materials, which in its facilities provide proper conditions for optimal pig growth (environmental monitoring, water, feeds, disposable systems, etc.).

This company complies with Regulations to the Control of raw materials in the U.S. Code of Federal Regulations (CFR), ICH, and other regulations/guidance's cited below: Regarding 21 CFR 211.110 Control of in-process materials, ICH Q5A/D for cell substrates and viral safety, ICH Q7 discussing the need to check with Appropriate materials specifications, ICH Q10 stating that a bio manufacturer is responsible for the quality of purchased materials.

In their facilities the pig receives ante and post-mortem inspections by the USDA and acceptance with the FDA in accordance with ISO 22442-2:2007 Medical devices utilizing animal tissues and their derivatives—Part 1: Application of risk management Part 2: Controls on sourcing, collection and handling.

In summary this company meets the following important aspects: adherence to regulations, quality systems emphasis, quality management, monitor/audit of the manufacturing process, aseptic techniques required during production, purity product and process-related impurities, maintenance of equipment, batch production and control records and maintenance of documentation.

In the new processes, to the previous patents by the inventor WO/2009/040768 and US20100135964, the company added to the final product the important value: Lyophilization or freeze-drying process.

Lyophilization, is a stabilization method that is widely used in the pharmaceutical industry for biological material. Lyophilization, or freeze-drying, is a complex and specialized drying technique and is the preferred method of drying biological tissues because can achieve very low levels of moisture, typically between 1 to 4% (Adams, 2007).

This process minimizes tissue shrinkage, deformation, solute concentration effects and thermal inactivation of proteins and enzymes that occur during drying by alternative heat-based methods. Because it operates within a closed system, particulate contamination is minimized (Adams, 2007).

Since the product is dried without excessive heating, proteins and other products that would be thermally denatured can be successfully preserved without loss of activity (Adams, 2007).

Because the water and oxygen have been removed from freeze-dried is, considered to be "shelf stable" or safe to store at room temperature for years. Microorganisms need water to survive, so if remove moisture from the material bacterial contamination is reduced (Adams, 2007).

Thus, the principle advantages of lyophilization as a drying process are: a. Minimum damage and loss of activity in delicate heat-liable materials. b. Product excellence: a well-dried product exhibits a long shelf life and maximum activity on rehydration, and c. Quality and regulatory assurance: consistency throughout batches is assured (Adams, 2007).

For the additional processes: a. Perforation was used Registered Firm AS9100 Rev. B, ISO 9001:2000 Certified b. Packaging and Sterilization: A United States FDA registered manufacturer. ISO 13485-2003 certified.

Derived from the processes of the present invention, which comply with all rules and regulations, is obtained from the porcine tunica serosa an ultra-thin and delicate, soft graft conformable material, single layer, transparent, with a defined pore size in their arrangement, with excellent flexibility, strength and breathability.

The isolated graft has reliability, manageability, ease of use and safety while also increasing efficiency and minimise side effects.

Example #3

Research & Development

This product has been validated in previous studies, where the safety and efficacy has been fully established in more than 1,500 patients (especially children) in skin regeneration in partial-thickness burns, so the background can be assumed a particular mechanism action matching by analogy with repair mechanisms at the level of the ocular surface (biological plausibility).

Product Available data demonstrate the absence of adverse effects in use (absence of allergic and antigenic response), who's source and manufacturing comply with international standards.

It provides structure for adequate epithelial cells migration and perform a natural guide for tissue repair, because assists the delicate balance of wound healing, manufactured with a small pore to allow interact whit fluid drainage.

Main advantages: —biocompatibility (absence of allergic and antigenic response); —it stimulates the reconstruction of tissue; —easy handling shortens the time required for surgery with consequent improved recovery prospects.

It is presented in this example a case series study of 1501 patients (of which 85% where children) with superficial and mid dermal burns admitted to the Public Hospital of the Government of Guatemala, in the township of Amatitlán, in the period from March 1997 to November 2011.

In this case study (unpublished), is document the experience with the use of the porcine serous membrane as a dressing to heal burn wounds.

This clinical research refers to an interventional study, open, without comparison group, to treat patients in a single center, to examine treatment variation and patient outcomes, including the effect of new management strategies, implementation of practice guidelines, and quality improvement initiatives.

It specifically refers to the use of this product in the management of 1501 patients (particularly children) with >10% Total Body Surface Area (TBSA) of partial thickness burns, using a standardized application protocol.

A central and critical principle of this treatment philosophy is the concept of minimal intervention at the wound site. In a significant number of cases (97%), a single and comprehensive preparation of the site and a single application of these products integrated into the human body for the first time, dramatically improve the recovery prospects and the aesthetic outcome.

Effects of Interventions

From the very beginning of this therapeutic regimen, the patient began to feel less pain.

Group more affected: minors of 10 years (Child Abuse and Neglect in many cases)

Causal agent of the injuries: 90% for warm liquids

A unique treatment in 97% of cases Two or more applications 3%

50% of the patients received attention after the fifth day of the event of the injury 96% Curative efficiency.

2% deepening of the initial injury 2% infection

In 77% of the cases the area of burn surface was a minor of 10%.

Decrease of the hospitable stay in 56%

Saving in the cost benefit of hospitalization Us. 1,443, 859.64 in ten years,

Common causes of burns from most to least common are: Scalding from steam or hot liquids, Touching hot objects and Fire/flame.

Most burn injuries occur at home (this applies to about 70% of scalds)

During the treatment period, the patient did not show any irritation or allergic reaction to this new dressing.

The dressing proved to induce healing on its own and peeling off was easy on day 7 by shower. In 97% of cases the burned area exhibited complete epithelialization a day five or six, so the patient was discharged on day 8 after burns wound treatment.

Example #4

A prospective, randomized, comparative trial in superficial, mid dermal, and mixed partial-thickness burns.

The purpose of this investigation was to determine the effectiveness of new biological membrane as compared with Duoderm® manufactured by ConvaTec, on the rate of wound re-epithelialization during dressing procedures in patients with acute superficial, mid dermal, and mixed partial-thickness burns injuries.

Study Setting

Participants for this study will be recruited from the National Hospital of Amatitlán, under the authority of the Ministry of Health and Social Security of the Government of Guatemala, in the period from Jun. 1, 1999 to Jul. 31, 2000.

The Institutional Review Board (IRB) approved protocol and informed consent document for the study before inclusion.

Study Design

The study was designed as a prospective, randomized, comparative and controlled trial.

Participants

Inclusion Criteria

The possible participants and their parents/caregivers will be notified of their eligibility to participate in this study by the medical team. Informed caregiver consent and child assent (for children 6 years and above) will be gained and then the investigator will randomize the patient to one of the two dressing treatment arms using a computerized random number.

Methods/Design

Patients aged 0 to 40 years with an acute partial thickness burn injury (superficial partial to deep partial thickness inclusive) will be eligible for the trial.

It should be emphasized that many patients with minor burns (Total Body Surface Area) were hospitalized derived from different social circumstances, values, beliefs, health care practices, cultural barriers or some issues: such as lack of transport for dressing changes, received inappropriate first aid (e.g. dirty water) and additionally by the high incidence in children of non-accidental burns and scalds, with suspected mistreatment and in other cases by severe malnutrition.

Assessment of burn size by use the Lund and Browder chart for % Total Body Surface Area.

Objectives: The primary objective was to determine the days until > or =90% re-epithelialization. The secondary objectives were to evaluate the number of dressing changes/local wound care required.

Types of Outcome Measures

Primary outcomes: time to complete wound healing and proportion of participants with completely healed wounds.

Secondary outcomes: Incidence of adverse events; Hospital length of stay; Change in wound size or deeper conversion; Incidence of infection; Cost and Quality of life.

Intervention

The estimate of healing was performed with the next set of data:

Visual evaluation of the results of the burns area. Excellent: Epithelium obtained is flat, vigorous. Good: Less than 5% of the area looks smaller than a one millimeter high. Regular: More than 5% of the area looks more than a more millimeter high. Poor: Significantly presence of contracture, more than two millimeters lifting.

A photograph a will be taken of a participant's burn wound at the beginning and the end, or when any new cure.

For statistical analysis of this prospective study and evaluate the significance statistic with 30 or fewer patients were used the Kruskal Wallis tests and Fisher Exact Test for the variables length of hospital stay and number of cures and for the variable aesthetic effects contingency tables and the Fisher Exact Test were developed. The standard error was set at 0.05 (Alpha-Probability value of type 1 error).

Results

Regarding the healing time and hospital stay in 27 patients (71% of the population) occurred in seven days or less for both groups, with shorter cure, the fifth days with the use of porcine membrane in 5 cases (29% of the population), in relation to 2 cases (9.5%) treated with Duoderm®.

Regarding cosmetic results, at different stages of the assessment, notes that at discharge results were similar, but there is a difference marginally significant at month with excellent results: 9 cases (53%) patients with porcine membrane and 5 cases (24%) treated with Duoderm®.

Likewise, in the sixth month the achievement population retrieve the results were excellent in 7 cases for the group of porcine membrane treatment (58%) against 5 of Duoderm® (31%).

The cost difference of the two membranes is quite significant: the porcine membrane (Q. 15. oo) is the fifth of the value of Duoderm® Q. 75. oo) resulting from useful for our population characterized by low socio-economic levels.

Example #4

Determination of Humoral Immune Response in Graft Recipients

Forty patients 30 days after treatment were tested for a humoral immune response to a porcine membrane by mean to precipitation antibodies and skin test evaluation. The precipitating antibodies were tested by immunodifussion in agar gel and skin test were done by intradermic application of 0.02 ml and evaluated at 10 minutes and at 48 hours.

The antigens were obtained by aqueous extracts in P.B.S. (Phosphate buffered saline) with pH 7.2.

The precipitating antibodies, the immediate and delayed skin test were negative in the 100% of the cases.

This study was conducted by the Dr. Roberto Maselli, Professor of Immunology of the Faculty of Medical Sciences (University of San Carlos of Guatemala) specialized in the University of Colorado, USA.

Example #5

From May 2014 has Begun the Study:

Evaluation of the efficacy and safety of new Serous membrane graft in the reconstruction and treatment of burns in the ocular surface at the National Unit of Ophthalmology in the "Roosevelt Hospital" in Guatemala City, which consists of a clinical trial to identify the role of a new membrane in the treatment of epithelial defect, prevention of symblepharon, vascularization and corneal opacity as well as decreasing pain and improving visual acuity in patients with severe eye burns.

Investigational Device:

Certified products are used, fully compatible with the requirements of the FDA in the United States, which in its manufacturing processes meet the quality management system of international standards ISO 9001: 2008, ISO 22442-2 ISO 9001: 2000 and ISO 13485-2003 and the requirements of Good Manufacturing Practices (GMP) that require regulatory systems.

Each serous membrane has a label, which reads: EPITHELIAL BIORREGENERADOR. PRODUCT FOR CLINICAL RESEARCH NOT FOR COMMERCIAL PURPOSES.

The protocol is prepared to see if the design is appropriate and collect information to conduct other studies in the future, respecting the rights of patients and the ethical principles of research involving human subjects, contents of the declaration of Helsinki and subsequent updates.

Product available data demonstrate the absence of serious adverse effects in use, at the level of skin and consistent action by analogy with repair mechanisms at the level of the ocular surface (biological plausibility).

The study is based on current knowledge and the information sought is an advance in scientific knowledge on the treatment of ocular surface, opening a research of new technology and new clinical applications.

To our knowledge, this work represents the first line of research for the regeneration of the ocular surface with the porcine serous membrane and are looking for perfecting the model for planning future actions.

General Purpose:

Assess, for the first time, if the use of the new serous membrane graft alters the natural history of ocular burns Grade II to V of the Classification of Dua, from a clinical point of view, and if this development is favored with regeneration of the ocular surface and decrease inflammation and the complications.

Comments and Reviews of Doctors Running the Study

Has verified the usefulness of the product, according to the previous experience, as to the best management of this new membrane at the site of placement for its resistance, relative to the amniotic membrane.

In anticipation of the results, the following table summarizes the application of the product as an implant with non-absorbable sutures, in two cases of symblepharon:

| # | Age | Name | Injury (day) | Day of attention | First Evaluation | Permanence of the membrane in the tissues | Reactions | Ophthalmologist Commentary |
|---|-----|------|--------------|------------------|------------------|-------------------------------------------|-----------|----------------------------|
| 1 | 9 | C. P. | 24 Dec. 2015 | Dec. 25, 2015 | No Adhesions-Membrane and sutures in situ. | 30 days | No | Good performance |
| 2 | 8 | H. P. | 1 Jan. 2015 | Jan. 1, 2015 | No Adhesions-Membrane | 45 days | No | Good performance |

The invention claimed is:

1. A method for inducing restoration of diseased or defective ocular tissues, said method comprising:
   applying a transparent biocompatible conjunctival implant as a graft in direct contact with a diseased or defective ocular surface of a patient's eye,
   wherein the conjunctival implant consists of porcine small intestinal serosa (or serous membrane),
   wherein the porcine small intestinal serosa (or serous membrane) of the conjunctival implant is utilized to induce restoration, remodeling, and repair of tissue in a variety of injuries or conditions in the cornea, the conjunctiva, and/or the eyelid due to trauma, diseases, or surgery.

2. The method of claim 1 wherein the conjunctival implant is an overlay graft, an inlay graft or combined inlay and overlay grafts to promote and protect ocular epithelial recovery.

3. The method of claim 1 wherein said restoration, remodeling, or repair of the ocular surface comprises the induction of connective and epithelial tissue repair at said diseased or defective ocular surface.

* * * * *